United States Patent
Gavalda Santapau et al.

(10) Patent No.: US 10,894,085 B2
(45) Date of Patent: Jan. 19, 2021

(54) SYSTEM FOR THERMOTHERAPY TREATMENT OR PREVENTION OF ANTIMICROBIAL RESISTANT OR BIOFILM INFECTIONS

(71) Applicants: FUNDACIÓ HOSPITAL UNIVERSITARI VALL D'HEBRON—INSTITUT DE RECERCA, Barcelona (ES); FUNDACIÓ INSTITUT DE BIOENGINYERIA DE CATALUNYA, Barcelona (ES); INSTITUCIÓ CATALANA DE RECERCA I ESTUDIS AVANÇATS, Barcelona (ES)

(72) Inventors: Joan Gavalda Santapau, Sant Pol de Mar (ES); Victor Franco Puntes, Barcelona (ES); Eduard Torrents Serra, Terrassa (ES)

(73) Assignees: FUNDACIÓ HOSPITAL UNIVERSITARI VALL D'HEBRON—INSTITUT DE RECERCA, Barcelona (ES); FUNDACIÓ INSTITUT DE BIOENGINYERIA DE CATALUNYA, Barcelona (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 0 days.

(21) Appl. No.: 16/078,836

(22) PCT Filed: Mar. 1, 2017

(86) PCT No.: PCT/IB2017/000186
§ 371 (c)(1),
(2) Date: Aug. 22, 2018

(87) PCT Pub. No.: WO2017/149378
PCT Pub. Date: Sep. 8, 2017

(65) Prior Publication Data
US 2019/0054172 A1    Feb. 21, 2019

Related U.S. Application Data

(60) Provisional application No. 62/301,946, filed on Mar. 1, 2016.

(51) Int. Cl.
| | | |
|---|---|---|
| A61K 41/00 | (2020.01) | |
| A61N 5/06 | (2006.01) | |
| A61K 47/69 | (2017.01) | |
| A61P 31/04 | (2006.01) | |
| A61N 5/10 | (2006.01) | |
| A61B 18/12 | (2006.01) | |
| A61N 7/00 | (2006.01) | |
| A61N 7/02 | (2006.01) | |

(52) U.S. Cl.
CPC ...... *A61K 41/0052* (2013.01); *A61K 47/6923* (2017.08); *A61K 47/6935* (2017.08); *A61N 5/0624* (2013.01); *A61P 31/04* (2018.01); *A61B 18/12* (2013.01); *A61N 7/00* (2013.01); *A61N 7/02* (2013.01); *A61N 2005/0659* (2013.01); *A61N 2005/1098* (2013.01)

(58) Field of Classification Search
None
See application file for complete search history.

(56) References Cited

U.S. PATENT DOCUMENTS

| | | | |
|---|---|---|---|
| 2005/0170004 A1* | 8/2005 | Rosenberger | A61K 9/145 |
| | | | 424/490 |
| 2008/0213189 A1 | 9/2008 | Lee et al. | |
| 2009/0181101 A1 | 7/2009 | Rademacher et al. | |

(Continued)

FOREIGN PATENT DOCUMENTS

| | | |
|---|---|---|
| WO | WO 2015/148726 A1 | 10/2015 |
| WO | WO 2015/157530 A2 | 10/2015 |
| WO | WO 2017/025104 A1 | 2/2017 |

OTHER PUBLICATIONS

Larson, Timothy A., Pratixa P. Joshi, and Konstantin Sokolov. "Preventing protein adsorption and macrophage uptake of gold nanoparticles via a hydrophobic shield." Acs Nano 6.10 (2012): 9182-9190.*

(Continued)

*Primary Examiner* — John Pak
*Assistant Examiner* — Daniel L Branson
(74) *Attorney, Agent, or Firm* — Squire Patton Boggs (US) LLP (57) ABSTRACT

The system comprises a support to receive a nanoparticle assembly (NPA) and to be conveyed towards a localized area of an organism infected or at risk to be infected by microorganisms; said nanoparticle assembly (NPA) comprising a plurality of nanoparticles (NPs) each one (NP) having a metal core and a surface surrounding said metal core, the metal core being reactable to thermal energy; and an energy unit (15) configured to apply at least one thermal shot on said localized area exposed to the nano-particle assembly, increasing the temperature of said localized area via the. nanoparticle assembly (NPA), so enabling a nanotheranostic multimodal antimicrobial therapy, wherein the metal core being made of silver, gold, iron or a mixture of silver and gold.

11 Claims, 8 Drawing Sheets

(56) References Cited

U.S. PATENT DOCUMENTS

| | | |
|---|---|---|
| 2009/0186060 A1 | 7/2009 | Hainfeld et al. |
| 2011/0123452 A1 | 5/2011 | Hainfeld |
| 2012/0046593 A1 | 2/2012 | Oraevsky et al. |
| 2012/0237605 A1 | 9/2012 | Messersmith et al. |
| 2013/0095039 A1 | 4/2013 | Lu et al. |
| 2014/0294909 A1 | 10/2014 | Green et al. |
| 2015/0072337 A1 | 3/2015 | Lapotko et al. |
| 2015/0125533 A1 | 5/2015 | Sallam et al. |
| 2016/0022976 A1 | 1/2016 | Peyman |

OTHER PUBLICATIONS

Mathuria, Jitendra Prasad. "Nanoparticles in Tuberculosis Diagnosis, Treatment and Prevention: A Hope for Future." Digest Journal of Nanomaterials & Biostructures (DJNB) 4.2 (2009).*
International Search Report dated Jun. 2, 2017 for Application No. PCT/IB2017/000186, 10 pages.
Antibiotics in Laboratory Medicine, $5^{th}$ Edition, 2005, Lippincott Williams & Wilkins, Baltimore, Maryland, pp. 365-440.
Chandra, Jyotsna, et al. "In vitro growth and analysis of *Candida* biofilms", Nature Protocols 2008, vol. 3, No. 12, pp. 1909-1924.
Methods for dilution antimicrobial susceptibility tests for bacteria that grow aerobically; approved standard—Seventh Edition, Jan. 2006, vol. 26, No. 2, M7-A7.

* cited by examiner

SYSTEM FOR THERMOTHERAPY TREATMENT OR PREVENTION OF ANTIMICROBIAL RESISTANT OR BIOFILM INFECTIONS

FIELD OF THE INVENTION

The present invention generally relates to the technical field of thermotherapy. More particularly, the present invention is in the technical field of thermotherapy to treat and prevent antimicrobial resistant and biofilm infections.

BACKGROUND OF THE INVENTION

Access to effective antibiotics is essential in all health systems. Their use has reduced childhood mortality and increased life expectancy, and they are crucial for invasive surgery and treatments such as cancer chemotherapy and solid organ transplantation. Antimicrobial Resistance (AMR) is a concept rather than a disease like in itself and despite its dramatic rising, is not given the same attention as acute infectious threats like SARS, Pandemic flu or Ebola, nor the same attention as the three major infectious diseases HIV, Tuberculosis and malaria. AMR is a serious global menace, affecting global economic, social and public health. The most recent World Economic Forum Global Risks reports have listed AMR as one of the greatest societal risks threats to human health.

Among the most important AMR bacteria in terms of causing infections in hospitalized patients are the so-called 'ESKAPE' pathogens. These are *E. faecium, S. aureus, K. pneumoniae, A. baumannii, P. aeruginosa*, and *Entembacter* spp. The most prominent threat of AMR is the rapidly rising tide of resistance among AMR, 'ESKAPE' bacteria that cause hospital-based infections in the last years. In addition to the ESKAPE pathogens, AMR *E. coli*, remains the main cause of mortality by severe septicaemia in hospitalized patients. In countries with high levels of MDR resistance, including resistance to carbapenems, and in the case of infections due to carbapenem resistant *P. aeruginosa* (MDR/XDR *P. aeruginosa* incidence 25-50%) only a few therapeutic options are available, among these are polymyxins. In these countries and in the case of MDR/XDR *P. aeruginosa*, presence of resistance to polymyxins or aminoglycosides is an important warning that options for the treatment of infected patients are becoming even more limited. Then, few antibiotics are effective enough for therapy. The antibiotics that still do work, frequently have major side effects, are less efficacious, or are very expensive (tigecycicline). AMR is not only costly in terms of human suffering but also in monetary terms. AMR currently claim at least 50,000 lives each year across Europe and the US alone and about 700,000 lives worldwide; at the estimated cost of more than 1.5 billion EUR or 35$ billion annually.

In addition to increased resistance to existing agents, there is a lack of new antibiotics in development. For many years, the pharmaceutical industry has been successfully churning out new antibacterial drugs. However, it is becoming more difficult to find novel antibiotics, and many large drug companies have withdrawn from antibiotic development programs because the process is extremely costly, and often fruitless. Alarmingly, existing antibiotics are losing their potency due to the spread of resistance at an alarming rate while few new antibiotics are being developed. Therefore, we are facing a paradoxical situation, as a perfect storm, with increased levels of resistant bacteria along with a descending trend in antibiotic development.

The spread of AMR bacteria could dramatically set back modern medicine to the dark age of the pre-antibiotic era; achievements in modern medicine, such as decrease in the safety of childbirth, caesarean sections, treatment of preterm babies, major or even dirty minor surgery, treatment of pneumonia, sexual transmitted diseases, organ transplantation and cancer chemotherapy, which we today take for granted, would not be possible without access to effective treatment for bacterial infections with antibiotics.

It is now acknowledged the urgent need for funding research relevant to developing new antibiotics and alternatives for treating AMR, increasing economic incentives for developing urgently needed antibiotics, besides different policies at different levels, both in the human and animal health sector, to preserve antibiotic effectiveness.

Moreover, difficult-to treat chronic infections associated with medical devices such as joint replacements and other types of orthopaedic instrumentation, prosthetic heart valves, pacemakers, implantable defibrillators, urinary catheters and stents, peritoneal dialysis catheters, intravascular catheters, cerebrospinal fluid shunts, breast implants, and vascular grafts and stents are common in today's medical practice. When these devices become infected, they must often be removed to successfully cure the associated infection. Device removal is associated with significant morbidity, cost, and, in some cases, mortality. Devices such as stents, shunts, prostheses, implants, endotracheal tubes, pacemakers, and various types of catheters, to name a few, have all been shown to support colonization and biofilm formation by different bacterial species or *Candida* spp. These bacterial species or *Candida* biofilms are 30 to 2,000 times more resistant than planktonic cells to antimicrobial agents.

It is known in the art the value of Nanotechnology that has provided the possibility of delivering drugs to specific cells using nanoparticles. Nanotechnology is defined as the "intentional design, characterization, production, and applications of materials, structures, devices, and systems by controlling their size and shape in the nanoscale range (1 to 100 nm). Because nanomaterials are similar in scale to biologic molecules and systems yet can be engineered to have various functions, nanotechnology is potentially useful for medical applications. The field of nanomedicine aims to use the properties and physical characteristics of nanomaterials for the diagnosis and treatment of diseases at the molecular level. Nanomaterials are now being designed to aid the transport therapeutic agents through biologic barriers; to gain access to molecules; to mediate molecular interactions; and to detect molecular changes in a sensitive, high-throughput manner. In contrast to atoms and macroscopic materials, nanomaterials have a high ratio of surface area to volume as well as tunable optical, electronic, magnetic, and biologic properties, and they can be engineered to have different sizes, shapes, chemical compositions, surface chemical characteristics, and hollow or solid structures. These properties are being incorporated into new generations of drug-delivery vehicles, some of which are currently undergoing clinical investigation or have been approved by the Food and Drug Administration (FDA) for use in humans.

It is known also in the art the value of Gold and Silver nanoparticles helping to image, diagnose and treat oncological and infectious diseases. Moreover, in the design of this object, its programmed disintegration is also planned, so the device is dismantled into safe ionic species after use, once their job is done, finally excreted by the body. Small Ag NPs, the size of proteins, are known to corrode and dissolve in vivo yielding Ag+ ions that induce ROS and interfere with respiration mechanisms of bacteria resulting in a very broad-spectrum antibiotic. Then, there would be a persistent bacterial synergism killing due to Ag+ plus the antibiotics.

Interest in hyperthermia as an adjunct to conventional oncology treatments has increased over the past two decades. Hyperthermia now refers to heating tumours, tissues, or systems to temperatures of up to 42° C., either to sensitize tissue to conventional treatments, or to induce tumour regression. However, hyperthermia as therapy dates back millennia: liquids heated to vapor on stones or bricks were used to treat what was probably breast cancer by the Egyptians, Greeks and Romans. Hyperthermia in modern medicine was first used by a gynecologist Frans Westermark in 1898 who achieved an excellent response in locally advanced cervical carcinomas by running hot water an intracavitary spiral tube. Subsequently, hyperthermia has been used in various medical settings.

Moderate hyperthermia (≤42° C.) increases tumor blood flow with oxygenation, and can thus act as a radiosensitiser by increasing oxygenation and as a chemosensitiser in the tumor bed; this is potentially how hyperthermia modifies angiogenesis. Hyperthermia also affects cellular processes through protein denaturation, protein folding, aggregation, and DNA cross-linking leading to disruption of biomolecular assemblies, induction of heat-shock proteins, and also disruption of cellular mechanisms promoting the onset of acidosis or apoptosis. Heat can be delivered via different mechanisms depending on the extent of application; for example, energy sources may include ultrasound, thermal chambers, laser light, near infrared light or radiotherapy.

Hyperthermia using nanoparticles is a novel concept that enables controlled heating of tumor tissue. Nanoparticle-based hyperthermia can have direct therapeutic effects and enhance drug delivery in a single therapy, making it a therapy with two advantages for cancer treatment. Nanoparticles provide an interesting mode of application for hyperthermia, because by concentrating the local heat source (the nanoparticles) within the tumor, heat-induced damage to healthy cells can, in theory, be minimized. In addition, nanoparticles provide a vehicle for delivering chemotherapeutic drugs to the tumor at the same time that hyperthermia is induced; such composite nanoparticles could take direct advantage of chemosensitization effects. Then, the efficiency of hyperthermia has been advanced by using nanoscale technologies. Specifically, gold-based nanoparticles (AuNPs), carbon-based nanoparticles (CNPs) and iron oxide nanoparticles (IONPs) appear to be the most promising nano-sized constructs for improving hyperthermia. Metallic nanomaterials including gold and silver nanocrystals and nanorods have been shown to generate localized hyperthermal heating through the absorption of incident optical radiation and surface plasmon relaxation. Heating of gold nanoparticles has also been demonstrated under radiofrequency (RF) fields; however, multiple heating mechanisms have been proposed and the degree to which the gold particles heat in the RF field is uncertain.

WO2015148726A1 discloses a coating that can be powered to release microbicidal agents to both ensure the prevention of infections, and avoid the development of antibiotic resistance. Silver ions are used for antimicrobial characteristics. Besides, reverse electrolysis allows the ions to be released for a sustained period of time, and then collected back onto the implant to avoid silver poisoning. A wireless reverse electrolysis system releases a sufficient amount of silver ions to break down biofilm surrounding a joint implant. By applying a modulated current waveform that has a net negative value to a conducting copper strip, the mirror current induced on the silver coating surface has a net positive flow, allowing ions to be released into surrounding tissue. The ability to induce electrolysis of silver ions to kill bacteria can be used to avoid post-operative infection.

WO2017025104A1 relates to a delivery device suitable for delivering a chemical substance, e.g. a medical device in the form of microcapsules comprising antifouling agent for marine paint. The delivery device comprises a closed cavity, the cavity is defined by an innermost wall surface, wherein at least a section of the inner wall surface constitutes an inner surface of a delivery membrane wherein the delivery membrane comprises an interpenetrating polymer network substrate comprising a host polymer and a guest polymer, where the guest polymer is interpenetrating the host polymer to form substantially continuous pathways within said host polymer.

None of the prior art documents discloses a nanoparticle assembly delivered on a support (e.g. a hydrogel, scaffold, etc.) intended to be placed at a localized area of a patient infected or at risk to be infected by microorganisms and activated via one or more thermal shots. Moreover, none of the prior art documents discloses the association of an antimicrobial agent attached to the nanoparticle surface, to act as aptamer of the localized area when a thermal shot is applied.

DESCRIPTION OF THE INVENTION

The present invention is directed to an advanced targeted thermotherapy antibiotic theranostics nanoparticle (NP) system and method for AMR and biofilm infections.

Present invention applies some of the principles explained above to treat or prevent multiresistant (MDR)/extreme resistant (XDR) bacterial infections or very difficult to treat or prevent biofilm infections.

To that end, embodiments of the present invention provide according to a first aspect a system for thermotherapy treatment or prevention of antimicrobial resistant or biofilm infections, the system comprising a support (e.g. a mesh, a vascular or urinary catheter, an hydrogel, a prosthesis, a stent, sutures, a thread, a wire, electrodes, or an endotracheal tube) configured to receive a nanoparticle assembly and to be conveyed towards a localized area of an organism infected or at risk to be infected by microorganisms; said nanoparticle assembly comprising a plurality of nanoparticles each one having a metal core and a surface surrounding said metal core, wherein the metal core being reactable to thermal energy; and an energy unit configured to apply at least one thermal shot (supply of thermal energy in a generally short period of time) on said localized area exposed to the nanoparticle assembly, increasing the temperature of said localized area to a given value via the nanoparticle assembly, so enabling a nanotheranostic multimodal antimicrobial therapy.

The metal core may be made of silver (Au), gold (Ag), a mixture thereof (Au/Ag), or even made of iron.

According to an embodiment, at least one antimicrobial agent is attached to the nanoparticle surface, said at least one antimicrobial agent by itself being configured to act as aptamer of the localized area.

According to an embodiment, the surface of each nanoparticle comprises a mPEG covering in order the nanoparticle not being recognized by the organism as a foreign body.

According to an embodiment, the system also includes a control unit configured to control that said increase of temperature of the localized area after the at least one thermal shot is applied not exceeds 40° C. It should be noted that the control unit can be an independent unit or can be integrated in the energy unit.

According to yet another embodiment, the nanoparticles comprise the metal core joint to the at least one antimicrobial agent.

The thermal shot may comprise any of near infrared energy, low-intensity pulsed ultrasound energy, low ultrasound energy, phototherapy, low voltage electric heating, low voltage electric heating with electrolysis or radiotherapy.

Embodiments of the present invention also provide according to a second aspect a method for thermotherapy treatment or prevention of antimicrobial resistant or biofilm infections, comprising conveying a support towards a localized area of an organism infected or at risk to be infected by microorganisms, said support including a nanoparticle assembly comprising a plurality of nanoparticles each one having a metal core (e.g. of silver, or gold, or combinations thereof, among others) and a surface surrounding said metal core, the metal core being reactable to thermal energy, and applying, by an energy unit, at least one thermal shot on said localized area exposed to the nanoparticle assembly, increasing the temperature of said localized area to a given value via the nanoparticle assembly, so enabling a nanotheranostic multimodal antimicrobial therapy.

According to an embodiment of the method, the cited increase of temperature of the localized area after the thermal shot is applied is controlled to not exceed 40° C.

The energy can be provided to the local area by different means: photonic, thermal conductive, electric current, ultrasound etc.

According to an embodiment, at least one antimicrobial agent is attached to said nanoparticle surface acting as aptamer of said localized area to be treated. The nanoparticles can comprise the metal core joint to the attached antimicrobial agent.

Moreover, the surface of each nanoparticle may also comprise a mPEG covering in order the nanoparticle not being recognized by the organism as a foreign body.

In most of the cases, a treatment involving the cited thermal shot will include several thermal shots, which are repeated after a period of time of a predetermined duration (usually comprised between 15 minutes to 8 hours) depending on the activity of the infection to be treated which is kept under control for detection of microbial growth. Preferably, the repetition of the thermal shot(s) is managed by the control unit which is operatively connected to the energy unit, either forming part of the latter or being an independent unit. The treatment can be applied in different, preferably consecutive, days.

The antimicrobial agent(s) that can be attached to the nanoparticle surface may have different effects versus gram-positive cocci, gram negative bacilli or antibacterial agents, and can be selected among the following mycobacteria drugs: antimicrobials aztreonam, aminoglycosides (amikacin, gentamicin, neomycin, netilmicin, streptomycin, tobramycin), carbapenems (doripenem, ertapenem, imipenem-cilastatin, meropenem), cephalosporins (cefepime, cefazolin, cefoxitin, cefixime, cefoperazone-sulbactam, cefotaxime, ceftazidime, ceftriaxone, cefuroxime, ceftalorine, ceftizoxime), clindamycin, fluorquinolones (ciprofloxacin, levofloxacin, moxifloxacin, ofloxacin), fusidic acid, glyco-, glycolipo-lipopeptides (dalbavancin, daptomycin, televancin, teicoplanin, vancomycin), linezolid, macrolides (azithromycin, clarithromycin), penicillins (amoxicillin, amoxicillin clavulanate, ampicillin, ampicillin-sulbactam, piperacillin, piperacillin-Tazobactam, ticarcillin, ticarcillin-clavulanate, temocillin, cloxacillin, dicloxacillin, methicillin, nafcillin, oxacillin, penicillin G) polymyxins (colistin, polymyxin B), tetracyclines (doxycycline, minocycline), sulfadiazine, trimethoprim+sulmethoxazole, tigecycline, fosfomycin, quinupristin+dalfopristin, chloramphenicol.

As per a particular embodiment of the proposed method, antimicobacterial agents as amikacin, capreomycin, clofazimine, etambutol, ethionamide, isoniazid, kanamycin, para-aminosalicylic acid, pyrazinamide, rifabutin, rifapentine or streptomycin are further included in the nanoparticle assembly.

The disclosed method can be used to treat or prevent or used as adjuvant therapy of antimicrobial/surgical therapy of difficult to treat infections as abscesses (cerebral, subdural empyema, epidural, pulmonary, pleural, hepatic, splenic, nephritic or perinephric, gynecological, intraperitoneal, muscular, subcutaneous), mediastinitis, acute and chronic osteomyelitis, diabetic foot infections, prosthetic infection (e.g. orthopedic implant—associated Infections, vascular graft infection, tracheal stent infection), lock therapy of long-term catheter-related bloodstream infections, chronic prostatitis, decolonization or disinfection of infected or colonized endotracheal tube or urinary catheters, Cerebrospinal Fluid Shunt and Drain Infections, Cellulitis, Necrotizing Fasciitis, and Subcutaneous Tissue Infections.

As per another embodiment the method is also suitable to be used to treat or prevent gram negative rod (GNR) bacterial infections caused by MDR/XDR *Pseudomonas aeruginosa*, MDR/XDR *Klebsiella pneumoniae*, MDR/XDR *Acinetobacter baumanii, Escherichia coli* and others GNR resistant to more than two class of antimicrobials. MDR gram positive cocci bacterial infections caused by methicillin-resistant *Staphylococcus aureus*. Furthermore, the method may be used to treat infections due to bacteria growing in biofilms, especially Coagulase-Negative Staphylococci, *Staphylococcus aureus* and *Pseudomonas aeruginosa*. Moreover, the method may be used to treat MDR or extreme resistant *Mycobacterium tuberculosis* or other atypical mycobacteria difficult to treat.

The proposed method can be used as unique treatment or prevention or would be an adjuvant or complement of the elective antimicrobial or surgical treatment of these AMR or biofilm infections which are very difficult to cure.

Therefore present invention is based on creating a targeted thermotherapy antibiotic theranostics nanoparticle to address AMR or biofilm infections. The invention is able to diagnose and treat different AMR infections in a few shots.

The invention provides a multifunctional method intended to carry sufficient amounts of drugs, having antimicrobial effects by itself, administering thermotherapy and serving as diagnostic contrast agent for imaging (X-ray, CT Scan, MRI). The nanoparticle core preferably consists on mixtures of Au—Ag NCs (alloys, core-shell and heterodimmers) of different size to tune the chemical stability (and therefore control silver corrosion) and biodistribution, as a function of treatment needs. These nanoparticles allow the attachment of different antibiotics at the nanoparticle surface, acting as aptamers, to "direct" it towards the desired microorganisms, and enable simultaneous multiple antimicrobial and thermal effects. Au—Ag functionalized nanoparticles carrying Vancomycin will target MDR/XDR gram-positive infections, MDR gram-negative ones loading Colistin or Amikacin and XDR Tuberculosis attaching Amikacin. It is known the value of Gold nanoparticles helping to image, diagnose and treat oncological diseases. Moreover, in the design of this object, its programmed disintegration is also planned, so the support is dismantled into safe ionic species after use, once their job is done, finally excreted by the body. Small Ag NPs, the size of proteins, are known to corrode and dissolve in vivo yielding Ag+ ions that interfere with respiration mechanisms of bacteria resulting in a very broad-spectrum antibiotic. Then, there would be a persistent bacterial synergism killing due to Ag+, the antibiotics and the effects of the hyperthermia.

In the presence of hyperthermia, Au, Ag or Au—Ag, from the nanoparticle itself, absorbs heat. In the case of hyperthermia, the Au, Ag or Au—Ag NPs will concentrate the heat source, intensifying the beneficial effects of hyperthermia, as increasing oxygenation, angiogenesis, induction of heat-shock proteins and finally the production of ROS that would induce DNA bacterial damage and death.

The invention is capable to diagnose and treat different AMR infections or very difficult to treat bacterial infections in a few shots (i.e. thermal energy transmitted to the nanoparticles in several thermal shots (the number of thermal shots depending of the type of infection) separated by a given interval of time).

The invention may carry sufficient amounts of drugs having antimicrobial effects, administering and activable by thermotherapy and the metal core serving as diagnostic contrast agent for imaging (X-ray, CT Sean, MRI).

In a particular embodiment, Gold (10 nm) and Silver (15 and 40 nm) nanoparticles are incubated with different antibiotics (amikacin and colistin). Different buffers are used to control surface and antibiotic molecule charge to control their electrostatic interaction. Conjugation is monitored with UV-VIS spectroscopy and Zpotential.

Besides, by means of the cited strategy the invention provides an evaluation of the efficacy of a multifunctional nanoparticle of a mixture Au-AgNPs or AuNp alone with antibiotics or Au/in different murine models of XDR bacterial infection trying to show that; first Thermonanoantibiotic improves drug targeting, and second drug targeting improves Thermonanoantibiotic therapy.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF THE INVENTION

Present invention provides a therapeutic multimodal system and method to treat or prevent AMR/XDR bacterial or biofilm infections.

According to an embodiment, the proposed system comprises a support (not illustrated in the figures) configured to receive a nanoparticle assembly NPA and to be conveyed towards a localized area of an organism of a living being infected or at risk to be infected by microorganisms. The nanoparticle assembly NPA comprises a plurality of nanoparticles NPs each one NP having a metal core and a surface surrounding said metal core, wherein the metal core being reactable to thermal energy. An energy unit 15 (see an example thereof on FIG. 2) is configured to apply at least one thermal shot (supply of thermal energy in a short period of time) on said localized area exposed to the nanoparticle assembly NPA, increasing the temperature of said localized area, so enabling the nanotheranostic multimodal antimicrobial therapy.

Figure 1:
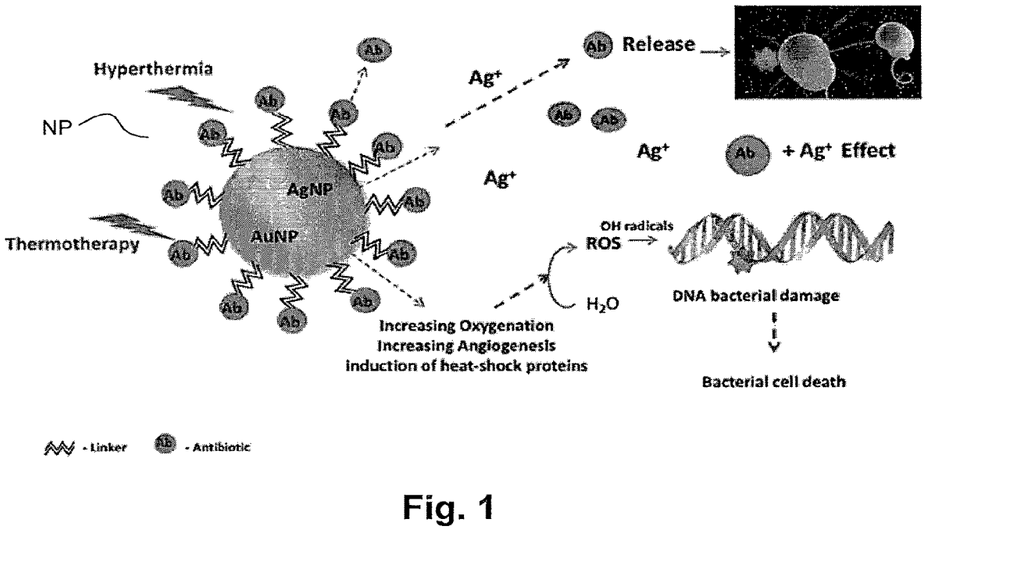
FIG. 1 is a schematic drawing showing an embodiment of the operating principle of this invention, i.e. nanotheranostic thermotherapy strategies to treat Antimicrobial Resistant Infections or biofilm infections. The nanoparticle according to this particular embodiment comprises an Au—Ag metallic core allowing the attachment of different antibiotics at the surface, acting as aptamers.

According to the embodiment of FIG. 1, the metal core is made of a mixture of gold and silver. According to other embodiments, in this case not illustrated, the metal cores are made of silver, gold or iron.

The proposed system preferably also comprises a control unit (not illustrated), at least connected to the energy unit 15, and being independent of the latter or integrated therein. The control unit being configured to control that the increase of temperature of the localized area after the at least one thermal shot is applied not exceeds 40° C. Moreover, the control unit may be also configured to control the repetition of the thermal shots separated by intervals of a given duration.

According to the embodiment of FIG. 1, the nanoparticles NPs also comprise attached to the surface one or more antimicrobial agents (antibiotics, Ab as illustrated in FIG. 1). The different antibiotics have the property of acting as aptamers. In alternative embodiments, not illustrated, the nanoparticles do not include any antibiotic.

The surface of each nanoparticle NP may also comprise a mPEG covering in order the nanoparticle NP not being recognized by the organism as a foreign body.

Figure 2:
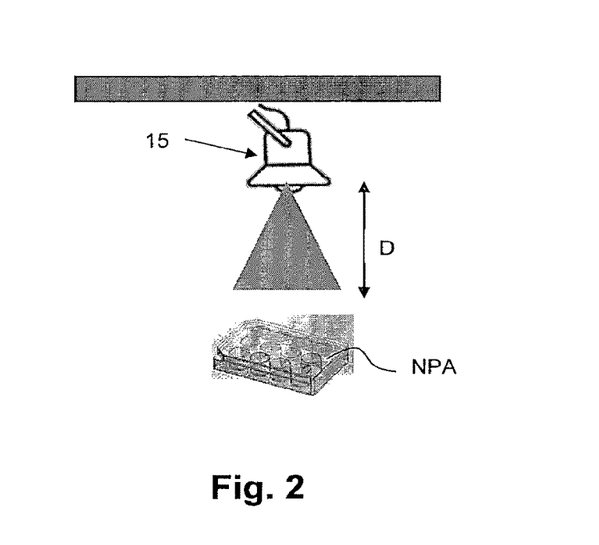
FIG. 2 is a schematic illustration of an embodiment of the proposed methodology for the application of the thermal shot, in this case, using phototherapy.

The thermal shot(s) may be applied by different strategies. For instance, via phototherapy (light) using a lamp or via heat (e.g. a hotplate) (as shown in FIG. 2). A low amperage direct electric current using a current power source plus sand bath can be also used. In this latter case, platinum electrodes are used.

The support on which the nanoparticles assembly NPA can be placed may include any of a mesh, a vascular or urinary catheter, a hydrogel, prosthesis, a stent, sutures, a thread, a wire, electrodes, or an endotracheal tube, among others.

Following a detailed description of different embodiments of the proposed method and preparation process of the nanoparticles will be made:

i) The invention develops a therapeutic multimodal strategy against antimicrobial resistant infections and difficult to treat infections due to bacterial biofilms by using a targeted thermotherapy nanotheranostic antimicrobial device. With this strategy a direct therapeutic effects in a multimodal therapy is obtained.

ii) Synthesis and Characterization of Silver Nanoparticles and Conjugation with Antibiotics Synthesis of silver nanoparticles (AgNP): AgNPs were prepared by seed-growth technique. A 100 mL of aqueous solution containing 5 mM of sodium citrate (SC) and 0.025 mM of tannic acid (TA) was prepared in a three-neck round-bottomed flask. The solution was heated with a heating mantle under vigorous stirring and a condenser to avoid evaporation of the solvent. After 5 min boiling, 1mL of silver nitrate ($AgNO_3$) at 25 mM was injected; the solution became bright yellow immediately. A 1 mL aliquot was extracted to characterization after 10 min vigorous stirring (g00).

Growth of silver nanoparticles: For the growth of AgNP from 10 nm to 20 nm (g01 and g02) the temperature of solution was cooled until 90° C. Then two cycles of 0.1 mL of SC (25 mM), 0.25 mL of TA (2.5 mM) and 0.25 mL of $AgNO_3$ (25 mM) were injected (time delay approx. 1 min). After 15 min, aliquots of 1 mL were extracted for further characterization. In all the process (synthesis and growth), AgNPs were stored under protection against light and in the original solution from the synthesis.

Nanoparticles conjugation with mPEG and antibiotics: Amikacin or colistin was used for the conjugation. Tetramethylannmonium hydroxide (TMAOH) (10 mM) was used as cationic surfactant; required to avoid aggregation of AgNPs. The resulting nanoparticles were purified by 2 cycles of centrifugation (20000 g during 20 min) at room temperature. The first pellet was resuspended with destilled water and the second pellet was resuspended in the same volume of TMAOH (10 mM). The solution was transferred into a glass vial and stirred employing a magnetic stirrer. Then, low volume of amikacin or colistin was added to achieve final concentration of 12.8 mg/L mixed with AgNPs. After 1 h under vigorous stirred at room temperature a mixed solution of mercapto-Polyethyleneglycol (mPEG) and amikacin or colistin was added. The final concentration of mPEG was 0.3 μM while the final concentration of antibiotic was 25.6 mg/L. After 30 min of vigorous stirring, the prepared solution was purified (20000 g during 20 min) and the pellet was resuspended to the original volume with distilled water.

Techniques: The characterization of each step of nanoparticles conjugated with amikacin or colistin were analyzed by UV-Vis spectrophotometry, the AgNP solution was placed in a cell, and spectral analysis was performed in the 300-800 nm range at room temperature. Dynamic Light Scattering (DLS) was used to measure the AgNP size. 1 mL of AgNP was placed in a cell, and DLS and Z Potential analysis were performed. The images of AgNPs were visualized using a Transmission Electron Microscopy (TEM). The prepared colloidal AgNPs were used for the size distribution measurements.

iii) Synthesis and Characterization of Gold Nanoparticles and Conjugation with Antibiotics Synthesis of gold nanoparticles: Gold nanoparticles (AuNP) were prepared by seeded-growth method. A 150 mL aqueous solution of SC (2.2 mM), 0.1 mL of TA 2.5 mM and 1 nnL of potassium carbonate ($K_2CO_3$, 150 mM) was added in a 250 mL three-neck round-bottomed flask. The solution was heated with a heating mantle under vigorous stirring. A condenser was utilized to prevent the evaporation of the solvent. 1 mL of precursor, tetrachloroauric acid ($HAuCl_4$, 25 mM) was injected after the temperature remained stable at 70° C. The color of the solution changed in less than 10 seconds to black-grey and then in the following 1-2 minutes to orange-red. The solution was stirring for 5 min at 70° C. more to complete reaction. The resulting particles (~3.5 nm, $7.10^{13}$ NPs/mL) were coated with negative charge and stable for weeks.

Growth of gold nanoparticles: Immediately after the synthesis of the Au seeds and in the same vessel, the sample was diluted extracting 55 mL and then, adding 55 mL of SC 2.2 mM.

Then, when the temperature remained stable at 70° C., 2 additions of 0.5 mL of $HAuCl_4$ (25 mM) were sequentially injected on a time interval 10 min. This growing step comprising sample dilution plus 2 injections of $HAuCl_4$ was repeated until the particles reached the desired size.

Nanoparticles conjugation with mPEG and antibiotics: the resulting nanoparticles were purified by centrifugation (15000 g during 15 min) at room temperature in 1 mL eppendorfs. The pellet was resuspended up to the original volume with TMAOH 10 mM.

The solution was transferred into a glass vial and stirred employing a magnetic stirrer. Then, small volume of colistin/amikacin was added to achieve final concentration of 12.8 mg/L mixed with AuNPs. After 1 h under vigorous stirred at room temperature a mixed solution of mPEG and antibiotic was added. The final concentration of mPEG was set to 0.3 μM while the final concentration of antibiotic was 25.6 mg/L.

Afterwards 30 min of stirring, the prepared solution was centrifugated (20000 g, 20 min) and the pellet was resuspended to the original volume with destilled water.

Techniques: Aliquots in each step were characterized by UV-Vis spectrophotometry.

iv) Bacterial Strain and Growth Conditions

For planktonic susceptibility studies, three extensively drug-resistant (XDR) clinical isolates of *P. aeruginosa* (Pa 1016; XDR strain harbouring an hiperproduction of AmpC, OprD, inactivation (Q142X), only susceptible to colistin and amikacin and isolate disseminated in Spanish hospitals (ST175), Pa46; XDR strain harbouring a VIM-2, only susceptible to colistin and amikacin (ST111) and Pa54; XDR strain harbouring a VIM-2, only susceptible to colistin and amikacin (ST111)) (Table 1), four XDR clinical isolates of *K. pneumoniae* (Kp1; XDR strain producing CTX-M and OXA-48, only susceptible to colistin, fosfomycin and amikacin, Kp2; XDR strain producing CTX-M and NDM, only susceptible to fosfomycin and colistin, Kp3; XDR strain producing a KPC carbapenemase, only susceptible to gentamycin and colistin and Kp4; XDR strain producing AmpC, only susceptible to colistin and amikacin) (Table 2) and three XDR clinical isolates of *A. baumannii* (Ab4256; isolate harbouring OXA-51 and OXA-24, only susceptible to XXX (ST38), AbII; isolate harbouring OXA-51, only susceptible to colistin, and tigecycline (ST103) and Abl4; isolate harbouring OXA-51, only susceptible to colistin, amikacin and tigecycline (ST2)) (Table 3), two *S. epidermidis* (SE14 and SE94) and two Methicillin-Resistant *S. aureus* (MRSA 15 and MRSA 16) were used.

For biofilm susceptibility studies, one laboratory biofilm-producing reference strain of *P. aeruginosa* (PA01) was used.

All strains were stored in skim milk at −80° C. in cryovial storage containers. Prior to each experiment, strains were subcultured in Trypticase Soy Agar for 24 h at 37° C. Then, cells from the subculture were suspended in Tryptic Soy Broth (TSB) or Mueller Hinton Broth (MHB) to reach a turbidity in the McFarland scale and subsequently the inoculum was adjusted to the desired concentration.

TABLE 1

Susceptibility of *Pseudomonas aeruginosa* strains.

| | | | | MIC (mg/L) and clinical category (CLSI breakpoint)[b] | | | | | |
|---|---|---|---|---|---|---|---|---|---|
| ID[a] | ST[c] | Profile | β-lactam resistant mechanism | CST | AMK | TOB | LVX | ATM | IP |
| Pa1016 | 175 | XDR | Hiperproduction AmpC, OprD, inactivation (Q142X) | 1 (S) | 2 (S) | 16 (R) | 128 (R) | 32 (R) | 16 |
| Pa46 | 111 | XDR | VIM-2 | 0.5 (S) | 16 (S) | 64 (R) | 32 (R) | 16 (I) | 256 |
| Pa54 | 111 | XDR | VIM-2 | 0.5 (S) | 16 (S) | 128 (R) | 32 (R) | 32 (R) | 256 |

[a]ID, strain identification number.
[b]CST, colistin; AMK, amikacin; TOB, tobramycin; LVX, levofloxacin; ATM, aztreonam; IPM, imipenem.
[c]ST, sequence type; S, susceptible; R, resistant; I, intermediate.

TABLE 2

Susceptibility of *Klebsiella pneumoniae* strains.

| Strain | Profile | β-lactam resistant mechanism | Antibiotic susceptibility and clinical category (CLSI breakpoint)[a] | | | | | | | | | | |
|---|---|---|---|---|---|---|---|---|---|---|---|---|---|
| | | | AMP | CAZ | FEP | IMP | MEM | CIP | GEN | AK | T/S | FOS | CST |
| Kp1 | XDR | CTX-M (Group 1) OXA-48 | R | R | R | R | R | R | R | S | R | S | S |
| Kp2 | XDR | CTX-M (Group 1) NDM | R | R | R | R | R | R | R | R | R | S | S |
| Kp3 | XDR | KPC | R | R | R | R | R | R | S | R | R | R | S |
| Kp4 | XDR | AmpC | R | R | R | R | R | R | S | R | S | R | S |

[a]S, susceptible; R, resistant; AMP, ampicillin; CAZ, ceftazidime; FEP, cefepime; IMP, imipenem; MEM, meropenem; CIP, ciprofloxacin; GEN, gentamicin; AK, amikacin; T/S, trimethoprim/sulfamethoxazole; FOS, fosfomycin; CST, colistin.

TABLE 3

Phenotypic and genotypic features of *Acinetobacter baumannii* isogenic strains.

| | Typing | | | | MIC values (mg/L) | | | | | | | | |
|---|---|---|---|---|---|---|---|---|---|---|---|---|---|
| Strain | Country | Clone | ST | SG | CAZ | FEF | IMP | MEM | CIP | LEV | GEN | AK | PIP |
| Ab14256 | Barcelona | B-R | 38 | 5 | <8 | 16 | 64 | >16 | 0.5 | <=1 | >8 | 8 | >64 |
| Ab1 | Israel | A | 103 | 12 | >=64 | >=64 | >=16 | >=16 | >=4 | 4 | >=16 | 21 | >=128 |
| Ab4 | Israel | C | 2 | 2 | >=64 | >=64 | >=16 | >=16 | >=4 | 4 | 4 | <=2 | >=128 |

| | MIC values (mg/L) | | | Aminoacidic changes | | | | | |
|---|---|---|---|---|---|---|---|---|---|
| Strain | T/S | CO | TIG | gyrA | parC | CHDL | MBLs | Other | AGLR |
| Ab14256 | <=2/38 | 0.25 | 0.5 | — | — | OXA-51 OXA-24 | | Ampc | aacA4 |
| Ab1 | >=320 | <=0.5 | 2 | S-83-L | normal | OXA-51 | NDM-2 | AmpC/ SAmpC | aph6A |
| Ab4 | 40 | <=0.5 | 4 | S-83-L | S-80-L | OXA-51/ S OXA-23 | — | AmpC/ SAmpC | aph6A |

ST: sequence type;
SG: sequence group;
CAZ, ceftazidime;
FEP, cefepime;
IMP, imipenem;
MEM, meropenem;
CIP, ciprofloxacin;
LEV, levofloxacin;
GEN, gentamicin;
AK, amikacin;
T/S, trimethoprim/sulfamethoxazole;
TIG: tigecycline;
CO: colistin.
Aminoacidic changes involved in high-level resistance to fluoroquinolones;
AGLR, resistance to aminoglycosides by aacA4/aph6A;
CHDL, class D carbapenem-hydrolizing β-lactamase.

v) Susceptibility Studies

The minimum inhibitory concentration (MIC) values were determined by broth microdilution method according to "Methods for Dilution Antimicrobial Susceptibility Tests for Bacteria That Grow Aerobically: Approved Standard M7-A7. CLSI, Wayne, Pa., USA, 2006" Colistin and amikacin free drugs were evaluated to compare the efficacy of nanoparticles. MIC was evaluated in Pa46, Pa1016, Kp1, Kp4, Ab14, Ab4256, MRSA 15, MRSA 16, SE14 an SE94 strains. ATCC *P. aeruginosa* 27853, ATCC *E. coli* 25922 and ATCC *A. baumannii* 19606 were used as quality control.

vi) Time-Kill Curve Assay

The efficacy of silver nanoparticles conjugated with amikacin on planktonic was evaluated in Pa46, Pa1016, Kp1, Kp4, Ab14 and Ab4256 strains. Time-kill curve assays were performed as previously described in ("Pillai Sea. Antimicrobial combinations. In V Lorian (ed.), Antibiotics in laboratory medicine, 5th ed. Lippincott Williams & Wilkins, Baltimore, Md. p. 365-440, 2005"). The concentrations of each antimicrobial agent tested alone were MIC, and nanoparticles were added at different volumes; 1 mL of nanoparticle and 2 mL of nanoparticle. A positive growth tube without antibiotics was used as a control. Test tubes were inoculated (final concentration, $5 \times 10^5$ colony forming unit (cfu)/ml) and incubated at 37° C.

The number of cfu/mL was determined at 4, 8 and 24 h of incubation. After 24 h at 37° C. viable count was then determined. The treatment was considered to have a positive bactericidal activity when a $\geq 3$ $\log_{10}$ reduction in the initial inoculums was reached.

vii) Thermal Shot Application vii. i) Thermal shot: Hyperthermia by Phototherapy (light) with AgNP Standarization:

The main objective was to find how much time was required to reach 40° C. in the medium of a 12-well plate using a light (energy unit) 15 as hyperthermia. The temperature of the medium was evaluated using the control unit. In its simplest example, a sensor thermometer can be used as control unit.

In the 12-well plate different volumes and mediums/treatments were tested: 2 mL of Mueller Hinton Broth (MHB) as a control, 1 ml_MHB plus 1 mL of AgNP and 1 mL MHB plus 1 mL of AgNP_AK as treatments. First of all, the plate was tempered 45 min at 37° C. and then, it was placed under light at a given distance D (preferably at about 45 cm of height). It was necessary 15 min to reach 40-41° C. in each well plate, independent of which medium were used (FIG. 2).

Application:

The efficacy of AgNPs conjugated with amikacin on planktonic using hyperthermia with Phototherapy (light) for the thermal shot application was evaluated in a high-risk clone (ST175) of *P. aeruginosa* (Pal 016).

Two plates were evaluated; one was at 37° C. (without phototherapy), and in the other phototherapy at different time points (T); T 1 h, T 1.5 h, T 2 h, T 2.5 h and T 3 h during 15 min was applied. After the phototherapy, an aliquot of the two plates was removed in order to determine viable cells and then the plates were put at 37° C. while waiting for the next heat stroke.

Initial inoculum was $1.0 \times 10^8$ cfu/mL and medium used for the experiments was MHB. In both plates (with or without phototherapy), there are the following groups: Growth control, Amikacin (at MIC), and AgNP_AK.

The treatment was considered to have a positive bactericidal activity when a. ?_3 $\log_{io}$ reduction in the initial inoculums was reached.

vii.ii) Thermal shot: Hyperthermia by Heat with AgNP Standarization:

The main objective was to find how much time was required to reach 40° C. in the medium of a 12-well plate using a heater as heat source (energy unit). The temperature of the medium was evaluated using the control unit. In its simplest example, a sensor thermometer can be used as control unit.

In the 12-well plate different volumes and mediums/treatments were tested: 2 mL of Mueller Hinton Broth (MHB) as a control, 1 mL MHB plus 1 mL of AgNP and 1 mL MHB plus 1 mL of AgNP_AK as treatments. First of all, the plate was tempered 45 min at 37° C. and then, it was placed on a heater (at 60° C.). It was necessary 15 min to reach 40-41° C. in each well plate, independent of which medium was used.

Application:

The efficacy of AgNps conjugated with amikacin on planktonic using hyperthermia by heat for the thermal shot application was evaluated in a high-risk clone (ST175) of *P. aeruginosa* (Pa1016).

Two plates were evaluated; one was at 37° C. (without heat), and in the other heat was applied at different time points (T); T 1 h, T 1.5 h, T 2 h, T 2.5 h and T 3 h during 15 min. After the heat stroke, an aliquot of the two plates was removed in order to determine viable cells and then the plates were put at 37° C. while waiting for the next heat stroke.

Initial inoculum was $1.0 \times 10^8$ cfu/mL and medium used for the experiments was MHB. In both plates (with or without heat), there are the following groups: Growth control, Amikacin (at MIC), and AgNP_AK.

The treatment was considered to have a positive bactericidal activity when a $\geq 3$ $\log_{io}$ reduction in the initial inoculums was reached.

Thermal shot: Hyperthermia by Low Amperage Direct Electric Current plus Sand Bath with AgNP Standardization:

The main objective was to find the amperage and how much time was required to reach 40° C. in the medium of a 12-well plate using electric current to achieve a rapid heat source. The temperature of the medium was also controlled.

Different volume (one, 1 mL (V); double, 2 mL (2V); and triple, 3 mL (3V)) of AgNP or AgNP_AK) was added in each well plate. For the control 2 mL TSB was used.

First, 12-well plate containing different volumes of medium/nanoparticles NPs, was tempered 30 min at 37° C. The plate was placed in a tempered sand bath at 75° C. and through two electrodes, low electric current (1-10 mA) were tested until the temperature reached 40° C. Then the plate was transferred to another sand bath (tempered sand bath at 43° C.), thereby maintaining the temperature of the plate at 40° C. for a period of time. It was necessary 10 mA and 1:30 minutes to reach 40-41° C. in each well plate in the first sand bath and, when the plate was put into the other sand bath, it maintained the 40° C. of the medium during 4 min.

Application:

vii.iii.i) Thermal shot: Hyperthermia by Low Amperage Direct Electric Current plus Sand Bath with AgNP in planktonic growth.

The efficacy of AgNPs conjugated with amikacin on planktonic using hyperthermia by Low Amperage Direct Electric Current plus Sand Bath for the thermal shot application was evaluated in a XDR *P. aeruginosa* (Pa1016), XDR *A. baumannii* (Ab14) and in a XDR *K. pneumoniae* (Kp1).

In a 12-well plate it was added at the same time 1 mL of inoculum (prepared with TSB to reach final concentration of $1.0 \times 10^8$ cfu/mL) plus 1 mL of AK alone, AgNP or AgNP AK (final volume of 2 mL). Plate was incubated at 37° C. during 30 min (while medium of the well was tempered at 37° C.), after that, the plate was placed in the first tempered sand bath (at 75° C.), and 10 mA of electric current during 1:30 min was applied in each well (electric current and time standardized to reach 40° C. in the medium (see vii.iii paragraph)).

Then the plate was transferred to a second sand bath (tempered at 60° C.) during 4 min; time that it was maintained the temperature at 40° C.

Four plates were evaluated; one was only at 37° C., other only with electric current application, other only in the sand bath and the last one with electric current application in the sand bath. Electric current was applied at different time points (T); T 1 h, T 2 h, and T 3 h. After the heat stroke, an aliquot of the four plates was removed in order to determine viable cells and then the plates were put at 37° C. while waiting for the next heat stroke (time between each heat stroke was 30 min).

The treatment was considered to have a positive bactericidal activity when a >3 $\log_{10}$ reduction in the initial inoculums was reached.

vii.iii.ii) Thermal shot: Hyperthermia by Low Amperage Direct Electric Current plus Sand Bath with AgNP in biofilm growth.

The efficacy of AgNPs conjugated with amikacin on silicone biofilm discs using hyperthermia by Low Amperage Direct Electric Current plus Sand Bath for the thermal shot application was evaluated in a reference biofilm-producing strain (PAO1).

For the experiment the silicone discs, the protocol described by Chandra et al. "In vitro growth and analysis of *Candida* biofilms" was followed with some small modifications. The bacteria were grown overnight in TSB at 37° C. The cultures were centrifuged, washed twice with sterile Phosphate Buffer Solution (PBS) and then re-suspended to a final concentration of 0.5 McFarland for adjusted to the final concentration of $1.0 \times 10^7$ cfu/mL. In each well of the 12-well plate 4 mL of inoculum was placed and silicone discs were added. After 90 min at 37° C. of incubation (adhesion step), discs were transferred in a new 12-well plate with 4 mL fresh TSB and then the plates were incubated again 24 at 37° C. and shaken at 60 rpm for growth biofilms.

The silicone discs were transferred in a new 12-well plate with treatment (final volume of 4 mL) 4: Amikacin, AgNP or AgNP_AK (3V). TSB were used to reach 4 mL in all the wells. Then the plate was placed in a tempered sand bath at 75° C. and the electric current (10 mA) was applied during 1:30 min. Following the plate is transferred to second sand bath during 4 min. This process is repeated up to three each 30 min, between heat shocks, plates were at 37° C.

Finally, after the three heat shots and after 24 hours, discs were transferred in a new plate with 4 mL of TSB and the discs were scraped. Colony counts were counted after 24 h at 37° C.

vii.iv) Thermal shot: Hyperthermia by Low Amperage Direct Electric Current plus Electrolysis with AuNP.

The efficacy of electrolysis thermal shot with gold nanoparticles (AuNP) to perform in planktonic cells was evaluated in Kp3 strain. This experiment was performed to evaluate the antimicrobial electrolysis effect with the activation AuNP in saline solution.

In a 12-well plate $5.10^5$ cfu/mL adjusted with NSS (0.9% of NaCl) and 1 mL AuNP was added. NSS was used as a control. The volume final in each well plate was 4 mL. Before the electric current the plate was tempered 30 min at 37° C. The assays tested were 2 mA during 1 min, 3 times in each well plate with the time delay 30 min between the shot. The same conditions were tested without electric current.

Results ii) Synthesis and Characterization of Silver Nanoparticles and Conjugation with Amikacin Size of the nanoparticles NPs using the seed-growth method started at 10 nm, and it increased to 20 nm through the growth steps. By means of the UV-Vis spectrum of 300-800 nm it was observed that the AgNP had an initial wavelength around 400 nm and increased slightly when the size increased.

Control nanoparticles, which were only conjugated with mPEG (AgNP_mPEG), have a larger size of about 25 nm.

Amikacin-conjugated nanoparticles (AgNP_AK) were larger than 25 nm. A maximum absorbance of 409 nm was observer in the UV-Vis spectrum range of 300-800 nm. The Z Potential presented a value of −46.6 mV.

iii) Synthesis and Characterization of Gold Nanoparticles and Conjugation with Antibiotics Size of the nanoparticles NPs using the seed-growth method started at 3.5 nm, and it increased to 20 nm through the growth steps. By means of the UV-Vis spectrum of 300-800 nm it was observed that the AuNP had an initial wavelength around 500 nm and increased slightly when the size increased.

Control nanoparticles, which were only conjugated with mPEG (AuNP_mPEG), have a larger size of about 5 nm. The UV-Vis spectrum showed a wavelength of 522 nm as well as Z Potential with a value of −43.1 mV.

AuNP_AK had a large-size, and the UV-Vis spectrum range of 300-800 nm was observed with a maximum absorbance of 523 nm. The Z Potential was −46.6 mV. Regarding the characteristics of of AuNP colistin, it had a large-size, and the UV-Vis spectrum range of 300-800 nm was observed with a maximum absorbance of 523 nm. The Z Potential was −29 mV.

v) Susceptibility Studies

The results of MIC susceptibility studies are shown in Table 4. MIC of amikacin decreased more than 3 concentrations when nanoparticle NP is conjugated with amikacin (AgNP_AK) in a XDR strain of *P. aeruginosa* (Pa46) and in Methicilllin-Resistant *S. aureus* (MRSA 15 and MRSA 16). The other strains decreased one or more concentration vs amikacin alone. AgNP_colistin obtained the same MIC of colistin alone in all strains in exception of *S. epidermidis* strains (SE14 and SE94), that decreased more than 3 concentrations respect colistin alone. Nanoparticles NPs without antibiotic (Amikacin or colistin) was not able to inhibit bacterial growth (in exception *S. epidermidis* strains, that reduced 3 concentrations).

TABLE 4

In vitro determination of the MIC in different clinical isolates strains using the broth microdilution method. Silver nanoparticles conjugated with amikacin (AgNP_AK).

| | MIC (mg/L) | | | | |
| --- | --- | --- | --- | --- | --- |
| | Amikacin | AgNP_AK | Colistin | AgNP_Coli | AgNP |
| Pa46 | 8 | 0.25 | 0.5-1 | 0.25-0.5 | >128 |
| Pa1016 | 0.5 | 0.25 | 0.5-1 | 0.25-0.5 | >128 |
| Kp1 | 2 | 0.25-0.5 | 1 | 0.25-0.5 | >128 |
| Kp4 | 1-2 | 0.25 | 0.125-0.25 | 0.25-0.5 | >128 |
| Ab14 | 1 | 0.5 | 1 | 0.5 | >128 |
| Ab4256 | 8 | 0.5 | 0.25 | 0.25-0.5 | >128 |
| MRSA15 | 8-16 | 0.5 | >128 | >128 | >128 |
| MRSA16 | 8-16 | 0.5 | 128->128 | >128 | >128 |
| SE14 | 1-2 | 0.25-0.5 | 32-64 | 0.06-0.125 | 32 |
| SE94 | 1 | 0.125 | 32 | 0.125 | 32 |

MIC, minimum inhibitory concentration;
Pa, *P. aeruginosa*;
Kp, *K. pneumoniea*;
Ab, *A. baumannii*;
MRSA, methicillin-resistant *S. aureus*;
SE, *S. epidermidis*.

vi) Time-Kill Curve Assay

Figure 3:
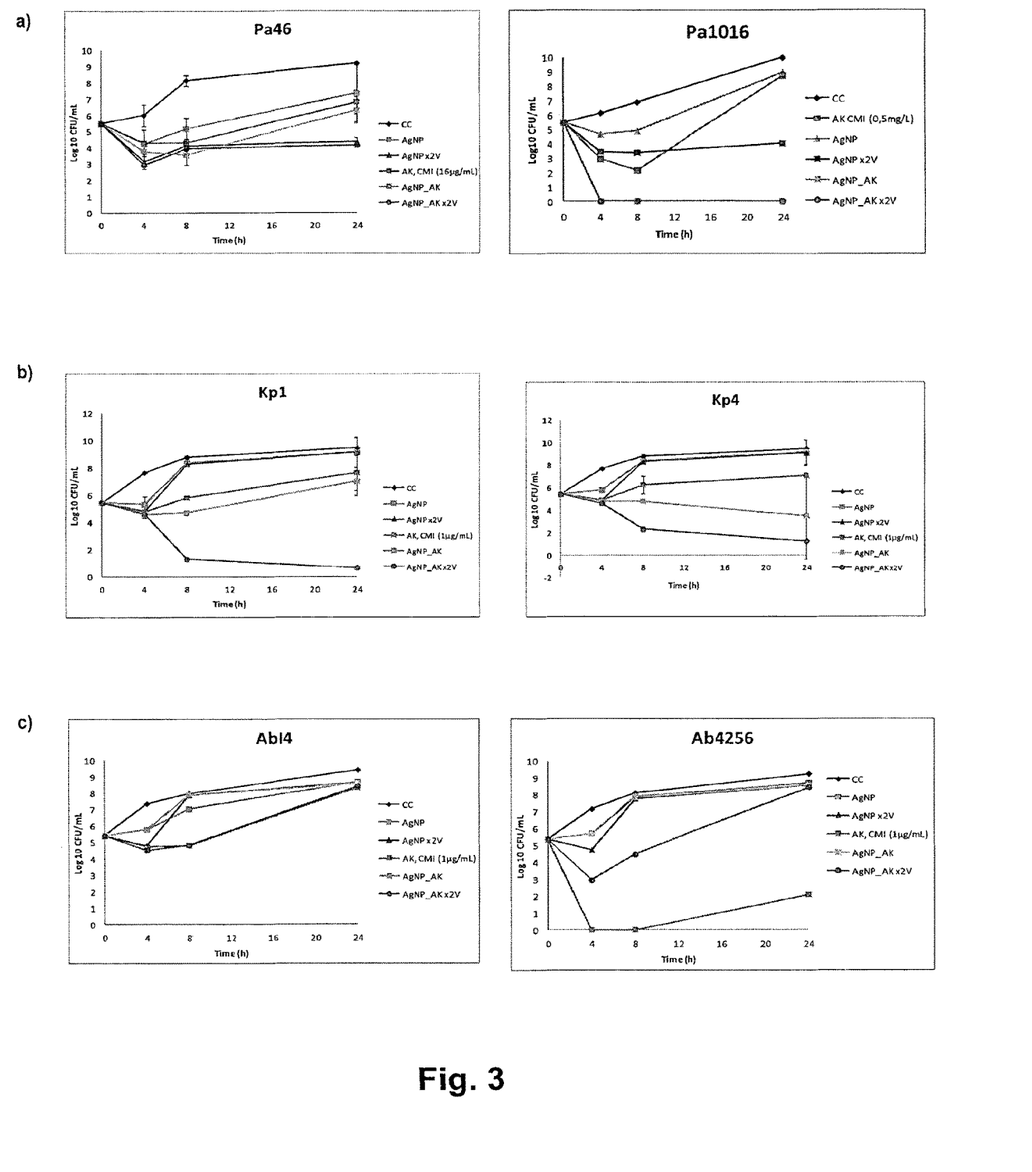
FIG. 3 illustrates the time-Kill Curve assays of AK, AgNP, AgNP_AK at 4, 8, and 24 h. (a) P. aeruginosa strains (b) K. pneumoniae strains and (c) A. baumannii strains.
Figure 4:
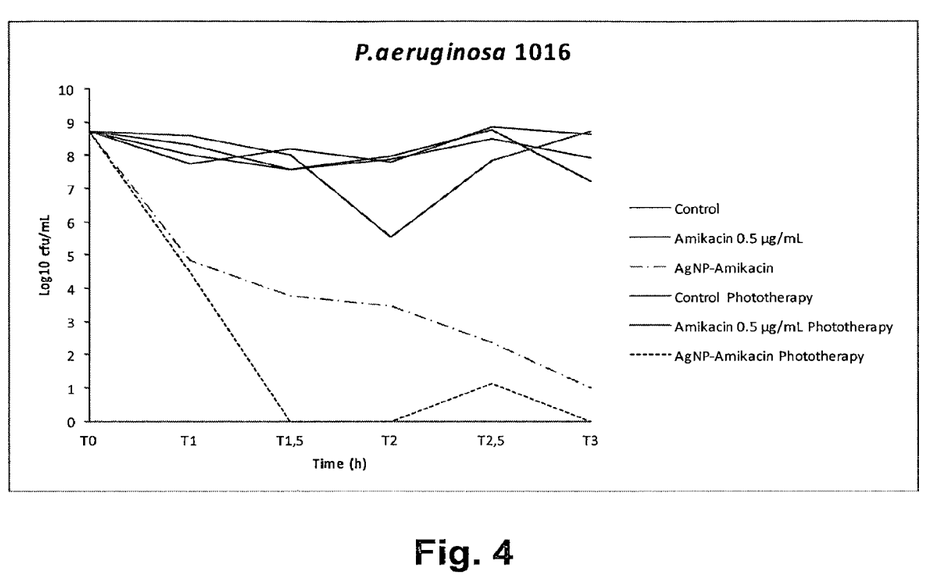
FIG. 4 illustrates the efficacy of AgNP_AK using hyperthermia by phototherapy (light) for the thermal shot application evaluated in a high-risk clone (ST175) of P. aeruginosa.

Time-kill curve assay (FIG. 3) showed a bactericidal effect for the high-risk clone (ST175) disseminated in Spanish hospitals (Pa1016) and *K. pneumoniae* strains treated with AgNP_AK at one and double volume at 4, 8 and 24 h. As well as these strains decreased more than 2 logarithms in viable counts respect to the other treatments. None of the two clinical strains of *A. baumannii* tested provided a favorable outcome at any time with the nanoparticle at different volumes. Drug-free nanoparticles (AgNp) had not any effect in none of the strains, even at one or two volumes.

vii) Thermal Shot Application vii.i) Thermal Shot: Hyperthermia by Phototherapy (Light) with AgNP The efficacy of AgNP conjugated with arnikacin on planktonic using hyperthermia by Phototherapy (light) for the thermal shot application was evaluated in a high-risk clone (ST175) of *P. aeruginosa* (Pa1016) (FIG. 4). At T 1.5 h, a strong decrease of $\log_0$ cfu/mL of viable bacteria of treatments with AgNP_AK was seen and both treatments had a bactericidal effect, nevertheless, AgNP_AK with phototherapy, achieved faster a negative culture compared to AgNP_AK.

The other groups (with or without phototherapy), did not decrease bacterial count versus growth control.

vii.ii) Thermal shot: Hyperthermia by Heat with AgNP

Figure 5:
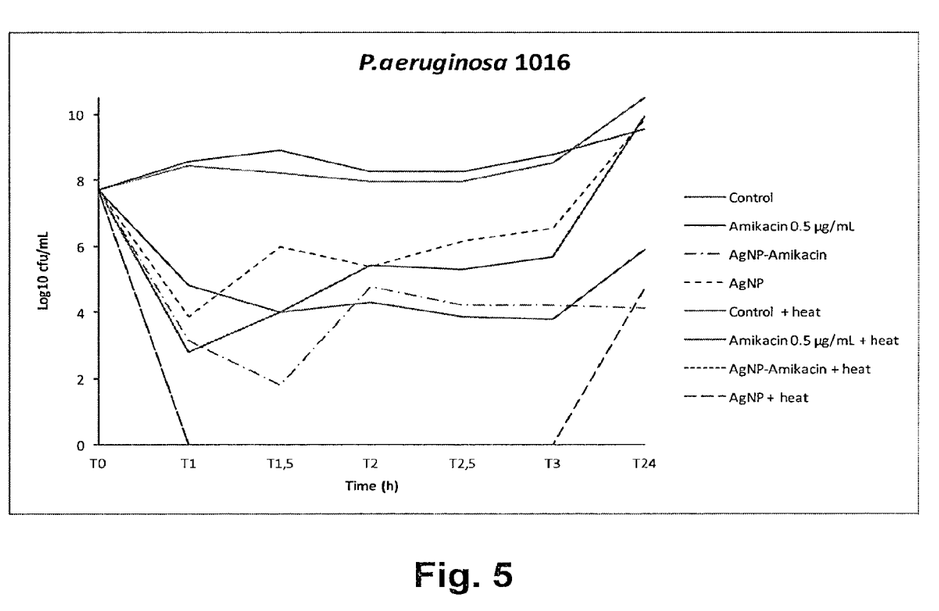
FIG. 5 illustrates the efficacy of AgNP_AK using hyperthermia by heat for the application of present invention evaluated in a high-risk clone (ST175) of P. aeruginosa.

The efficacy of AgNPs conjugated with amikacin on planktonic using hyperthermia by heat for the thermal shot application was evaluated in a high-risk clone (ST175) of *P. aeruginosa* (Pa1016) (FIG. 5). At T 1.5 h, a strong decrease of $\log_{ta}$ cfu/mL of viable bacteria of treatments with AgNP and AgNP_AK using hyperthermia was observed and both treatments had a bactericidal effect, nevertheless, AgNP_AK with heat, eradicated bacterial counts until 24 h, while AgNP regrowth between the 3rth heat stroke and the 24 h.

vii.iii) Thermal shot: Hyperthermia by Low Amperage Direct Electric Current plus Sand Bath with AgNP vii.iii.i) Thermal shot: Hyperthermia by Low Amperage Direct Electric Current plus Sand Bath with AgNP in planktonic growth.

Figure 6:
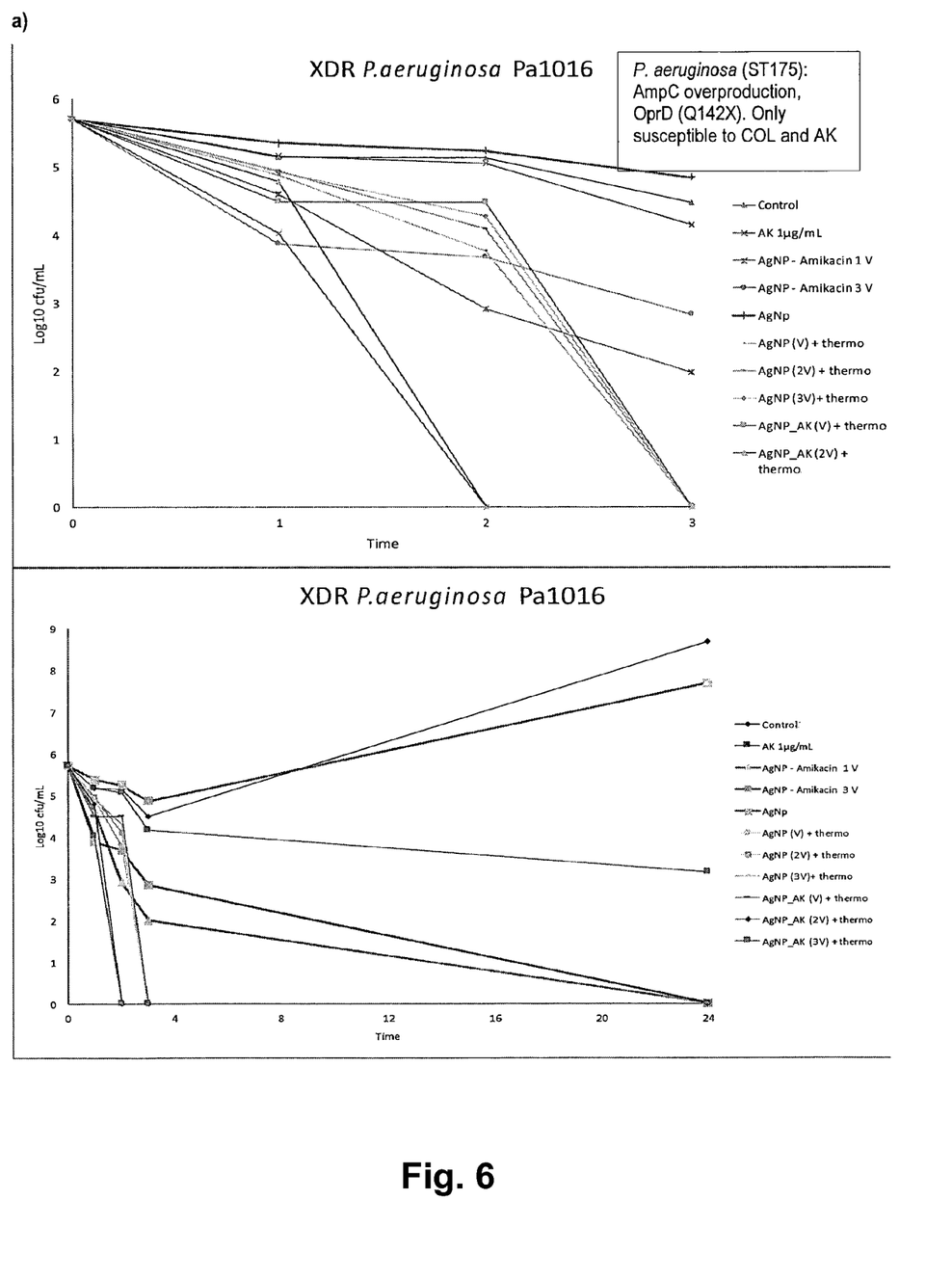
FIG. 6 illustrates the efficacy of AgNP_AK using hyperthermia by low amperage direct electric current plus sand bath which was evaluated in a) XDR P. aeruginosa (Pa 1016), b) XDR A. baumannii (Ab14), and c) XDR K. pneumoniae (Kp1) strains. In all of the images, first figure represent the enlarged graph CI rst until 3EC and 2nd is until 24 h).

The efficacy of AgNPs conjugated with amikacin on planktonic using hyperthermia by low amperage direct electric current plus sand bath was evaluated in a XDR *P. aeruginosa* (Pa 1016), XDR *A. baumannii* (Abl4), and in a XDR *K. pneumoniae* (Kp1) strains (FIG. 6). In Pa1016 and Kp1, two heat shocks were needed to negativist the bacterial count (maintained at 24 h), and in Abl4, with the first heat shock bacterial count was negativist. In the control plates with only at 37° C., only sand bat and, only electrical current, no differences was seen between molecules and the effect of the different groups.

vii.iii.ii) Thermal shot: Hyperthermia by Low Amperage Direct Electric Current plus Sand Bath with AgNP in biofilm growth.

Figure 7:
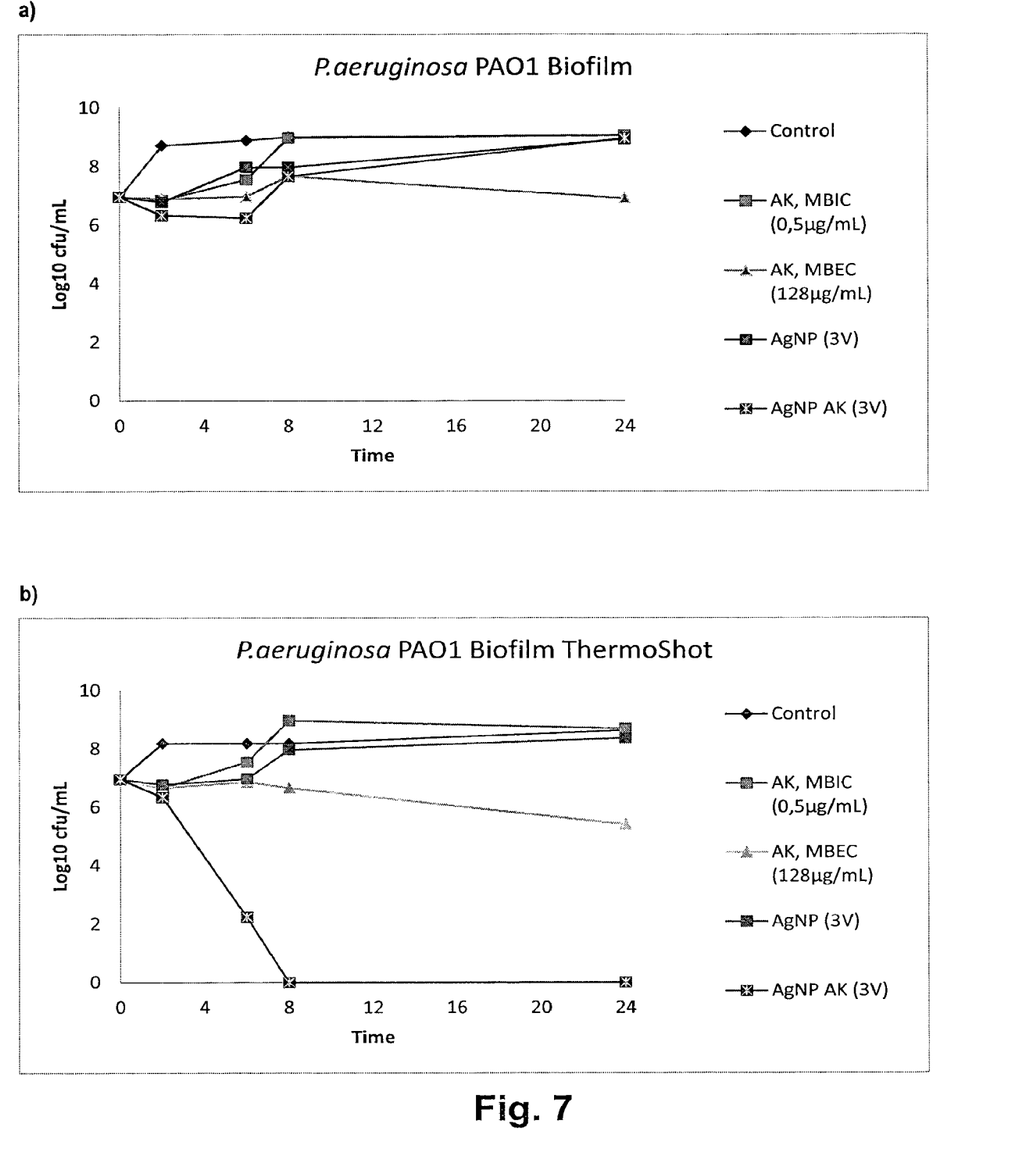
FIG. 7 illustrates the efficacy of AgNP_AK using hyperthermia by low amperage direct electric current plus sand bath which was evaluated in PAO1 strain. a) treatment groups in one of the control (plate at 37° C.) and b) treatment groups in the ThermoShot plate; hyperthermia with EC plus sand bath.

The efficacy of AgNPs conjugated with amikacin on silicone biofilm discs using hyperthermia by Low Amperage Direct Electric Current plus Sand Bath for the thermal shot application was evaluated in a reference biofilm-producing strain (PAO1) (FIG. 7). First 18 a represented the plate without heat shock (is the control plate of tempered at 37° C.), there was no differences between molecules and the effect of the different groups. Nevertheless, the same treatments in the plate applying electric current plus sand bath achieved negative cultures at 8 h and it maintained during 24 h.

vii.iv) Thermal shot: Hyperthermia by Low Amperage Direct Electric Current plus Electrolysis with AuNP.

Figure 8:
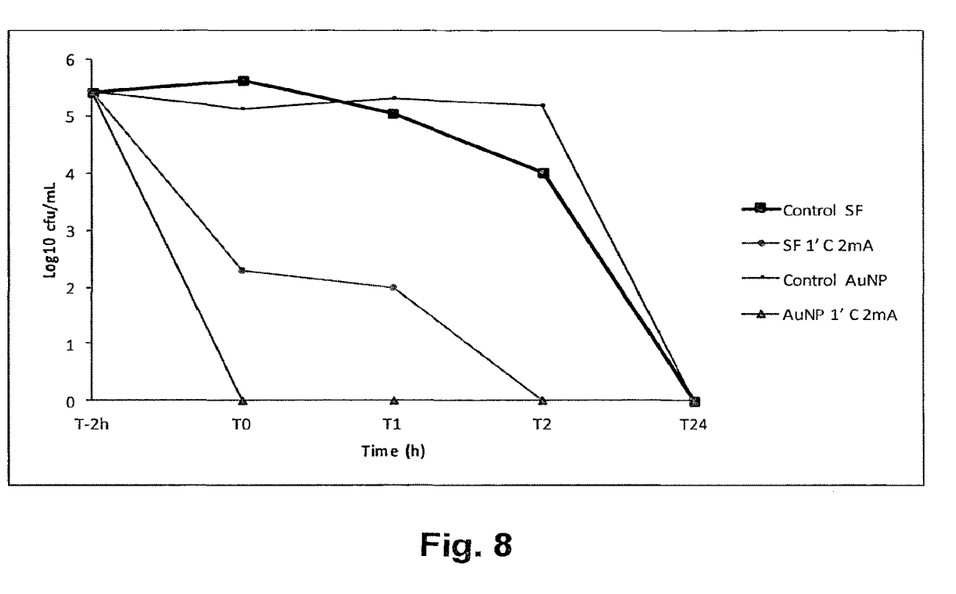
FIG. 8 illustrates the efficacy of AgNP_AK using hyperthermia by low amperage direct electric current plus electrolysis which was evaluated in Kp3 strain.

The efficacy of AgNPs conjugated with amikacin on silicone biofilm discs using hyperthermia by Low Amperage Direct Electric Current plus electrolysis the thermal shot application was evaluated in Kp3 strain (FIG. 8). AuNP with NSS and applying an electric current of 2 mA during 1 min, it was capable to achieved negative cultures after the first electric current, and it was maintained during the next 24 h.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein.

The scope of protection of present invention is defined in the following set of claims.

The invention claimed is:

1. A system for thermotherapy treatment of antimicrobial resistant or biofilm infections, the system comprising:
    a support configured to receive a nanoparticle assembly (NPA) and configured to be conveyed towards a localized area of an organism infected by microorganisms;
    said NPA comprising a plurality of nanoparticles each one nanoparticle having a silver core and a surface surrounding said silver core, wherein the silver core being reactable to thermal energy; and wherein the nanoparticles have attached on the surface at least the antimicrobial agent amikacin and wherein the surface of each nanoparticle comprises a mPEG covering;
    an energy unit configured to apply at least one thermal shot on said localized area exposed to the NPA, increasing the temperature of said localized area to a given value via the NPA, so enabling a nanotheranostic multimodal antimicrobial therapy.

2. The system, according to the claim 1, further comprising a control unit configured to control that said increase in temperature of the localized area after the at least one thermal shot is applied to not exceeds 40° C.

3. The system, according to claim 1, wherein said thermal shot comprises one of near infrared energy, low-intensity pulsed ultrasound energy, low ultrasound energy, phototherapy, low voltage electric heating, or low voltage electric heating with electrolysis or radiotherapy.

4. The system, according to claim 1, wherein the support includes at least one of a mesh, a vascular or urinary catheter, an hydrogel, a prosthesis, a stent, sutures, a thread, a wire, electrodes, or an endotracheal tube.

5. A method of thermotherapy treatment of antimicrobial resistant or biofilm infections in a patient infected, the method comprising:
    conveying to a localized area of an organism infected by microorganisms a support configured to be conveyed towards the localized area, the support configured to receive a nanoparticle assembly (NPA) and the support comprising the NPA comprising a plurality of nanoparticles each one having a silver core and a surface surrounding the silver core, wherein the silver core is reactable to thermal energy; and wherein the nanoparticles have attached on the surface at least the antimicrobial agent amikacin and wherein the surface of each nanoparticle comprises a mPEG covering; and
    applying, by an energy unit, at least one thermal shot to the localized area, increasing the temperature of said localized area to a given value via the NPA, so enabling a nanotheranostic multimodal antimicrobial therapy.

6. The method for thermotherapy treatment of antimicrobial resistant or biofilm infections according to claim 5, wherein said increase of temperature of the localized area after the thermal shot is applied being controlled to not exceed 40° C. by a control unit.

7. The method for thermotherapy treatment of antimicrobial resistant or biofilm infections according to claim 5, wherein the thermal shot is repeated after a period of time of a predetermined duration.

8. The method for thermotherapy treatment of antimicrobial resistant or biofilm infections according to claim 7, wherein said predetermined duration being comprised between 15 minutes and 8 hours.

9. The method for thermotherapy treatment of antimicrobial resistant or biofilm infections according to claim 5, wherein the thermal shot comprises one of near infrared energy, low-intensity pulsed ultrasound energy, low ultrasound energy, phototherapy, low voltage electric heating, or low voltage electric heating with electrolysis or radiotherapy.

10. The method for thermotherapy treatment of antimicrobial resistant or biofilm infections according to claim 5, wherein the support includes at least one of a mesh, a vascular or urinary catheter, an hydrogel, a prosthesis, a stent, sutures, a thread, a wire, electrodes, or an endotracheal tube.

11. The method for thermotherapy treatment of antimicrobial resistant or biofilm infections according to claim 5, further comprising including one or more antimicrobial agents comprising capreomycin, clofazimine, etambutol, ethionamide, isoniazid, kanamycin, para-aminosalacylic acid, pyrazinamide, rifabutin, rifapentine, or streptomycin in nanoparticle assembly.

\* \* \* \* \*